(12) United States Patent
Komoro

(10) Patent No.: US 11,304,599 B2
(45) Date of Patent: Apr. 19, 2022

(54) ENDOSCOPE HAVING ELECTROMAGNETIC SHIELD

(71) Applicant: HOYA CORPORATION, Tokyo (JP)

(72) Inventor: Atsushi Komoro, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 262 days.

(21) Appl. No.: 16/627,844

(22) PCT Filed: Aug. 22, 2018

(86) PCT No.: PCT/JP2018/030932
§ 371 (c)(1),
(2) Date: Dec. 31, 2019

(87) PCT Pub. No.: WO2019/044609
PCT Pub. Date: Mar. 7, 2019

(65) Prior Publication Data
US 2020/0178779 A1    Jun. 11, 2020

(30) Foreign Application Priority Data

Aug. 30, 2017    (JP) .............................. JP2017-166130

(51) Int. Cl.
*A61B 1/05* (2006.01)
*H04N 5/225* (2006.01)

(52) U.S. Cl.
CPC ........... *A61B 1/051* (2013.01); *H04N 5/2253* (2013.01); *H04N 2005/2255* (2013.01)

(58) Field of Classification Search
None
See application file for complete search history.

(56) References Cited

U.S. PATENT DOCUMENTS

| 9,285,582 B2 | 3/2016 | Ito et al. |
| 10,512,433 B2 | 12/2019 | Ikemoto et al. |

(Continued)

FOREIGN PATENT DOCUMENTS

| JP | 2001-104247 A | 4/2001 |
| JP | 2001-178675 A | 7/2001 |

(Continued)

OTHER PUBLICATIONS

International Search Report issued in International Bureau of WIPO Patent Application No. PCT/JP2018/030932, dated Nov. 6, 2018.

*Primary Examiner* — John P Leubecker
(74) *Attorney, Agent, or Firm* — Greenblum & Bernstein, P.L.C.

(57) ABSTRACT

An endoscope includes an objective lens provided at a distal end portion of an insertion portion, an image sensor in which a light receiving area is formed on a surface facing the objective lens, and a drive circuit substrate that is disposed on a back side of the image sensor and includes a drive circuit to drive the image sensor, the endoscope further including an electromagnetic shield that houses the image sensor and the drive circuit substrate, in which the electromagnetic shield includes: a first shield member including a cylinder that covers a side portion of the image sensor, a structure that is disposed between the image sensor and the objective lens and that has an opening that allows entrance of light from the objective lens, and a wiring pattern that is formed on an inner peripheral surface of the cylinder and the structure.

9 Claims, 7 Drawing Sheets

(56) References Cited

U.S. PATENT DOCUMENTS

| | | | |
|---|---|---|---|
| 2005/0035421 A1* | 2/2005 | Kayanuma | H04N 5/2253 257/432 |
| 2012/0155854 A1* | 6/2012 | Huang | H01L 27/14623 396/535 |
| 2013/0028589 A1* | 1/2013 | Zung | G02B 7/021 396/529 |
| 2015/0146073 A1* | 5/2015 | Kim | H04N 5/2257 348/335 |
| 2016/0358964 A1 | 12/2016 | Yoneyama et al. | |
| 2017/0311785 A1* | 11/2017 | Fujimori | A61B 1/04 |

FOREIGN PATENT DOCUMENTS

| | | |
|---|---|---|
| JP | 3875505 B2 | 1/2007 |
| JP | 2007-307238 A | 11/2007 |
| JP | 5377085 B2 | 12/2013 |
| JP | 2015-039410 A | 3/2015 |
| WO | 2015/125777 A1 | 8/2015 |

* cited by examiner

ENDOSCOPE HAVING ELECTROMAGNETIC SHIELD

TECHNICAL FIELD

The present invention relates to an endoscope.

BACKGROUND ART

An endoscope is used to examine a patient's body. The endoscope includes an insertion tube to be inserted into the body, and the insertion tube has, at its distal end, a distal end portion storing an image sensor.

Conventionally, in a case where an image sensor with an electrode extraction pad (bonding pad) on the light receiving side is incorporated into a distal end portion of an endoscope, wire extraction is performed by wire bonding or TAB, cable connection is performed after packaging, and then, the image sensor is inserted into a shield frame to ensure electromagnetic compatibility.

CITATION LIST

Patent Literature

Patent Literature 1: JP 5377085 B2
Patent Literature 2: JP 3875505 B2

SUMMARY OF INVENTION

Technical Problem

However, the conventional method of extracting the electrode by wire bonding has a disadvantage of necessity to provide a separate bonding pad around the chip, causing enlargement of the package.

On the other hand, the method of extracting the wires by TAB reduces the flying lead width in order to adapt to the recent narrow pitch arrangement of bonding pads, which has a disadvantage of deterioration in bending resistance.

The present invention has been made in view of such circumstances, and aims to provide an endoscope capable of extracting wires from a bonding pad formed on a light receiving side of an image sensor without using wire bonding or TAB.

Solution to Problem

An endoscope according to an aspect of the present invention includes an objective lens provided at a distal end portion of an insertion portion, an image sensor in which a light receiving area is formed on a surface facing the objective lens, and a drive circuit substrate that is disposed on a back side of the image sensor and includes a drive circuit to drive the image sensor, the endoscope further including an electromagnetic shield that houses the image sensor and the drive circuit substrate, wherein the electromagnetic shield includes: a first shield member including a cylinder that covers a side portion of the image sensor, a structure that is disposed between the image sensor and the objective lens and that has an opening that allows entrance of light from the objective lens, and a wiring pattern that is formed on an inner peripheral surface of the cylinder and the structure and provided to electrically connect the image sensor and the drive circuit substrate; and a second shield member externally fitted on a rear end side of the first shield member.

Advantageous Effects of Invention

According to the present application, it is possible to extract wires from the bonding pad formed on the light receiving side of the image sensor without using wire bonding or TAB.

DESCRIPTION OF EMBODIMENTS

Hereinafter, the present invention will be specifically described with reference to the drawings illustrating embodiments of the invention.

First Embodiment

Figure 1:
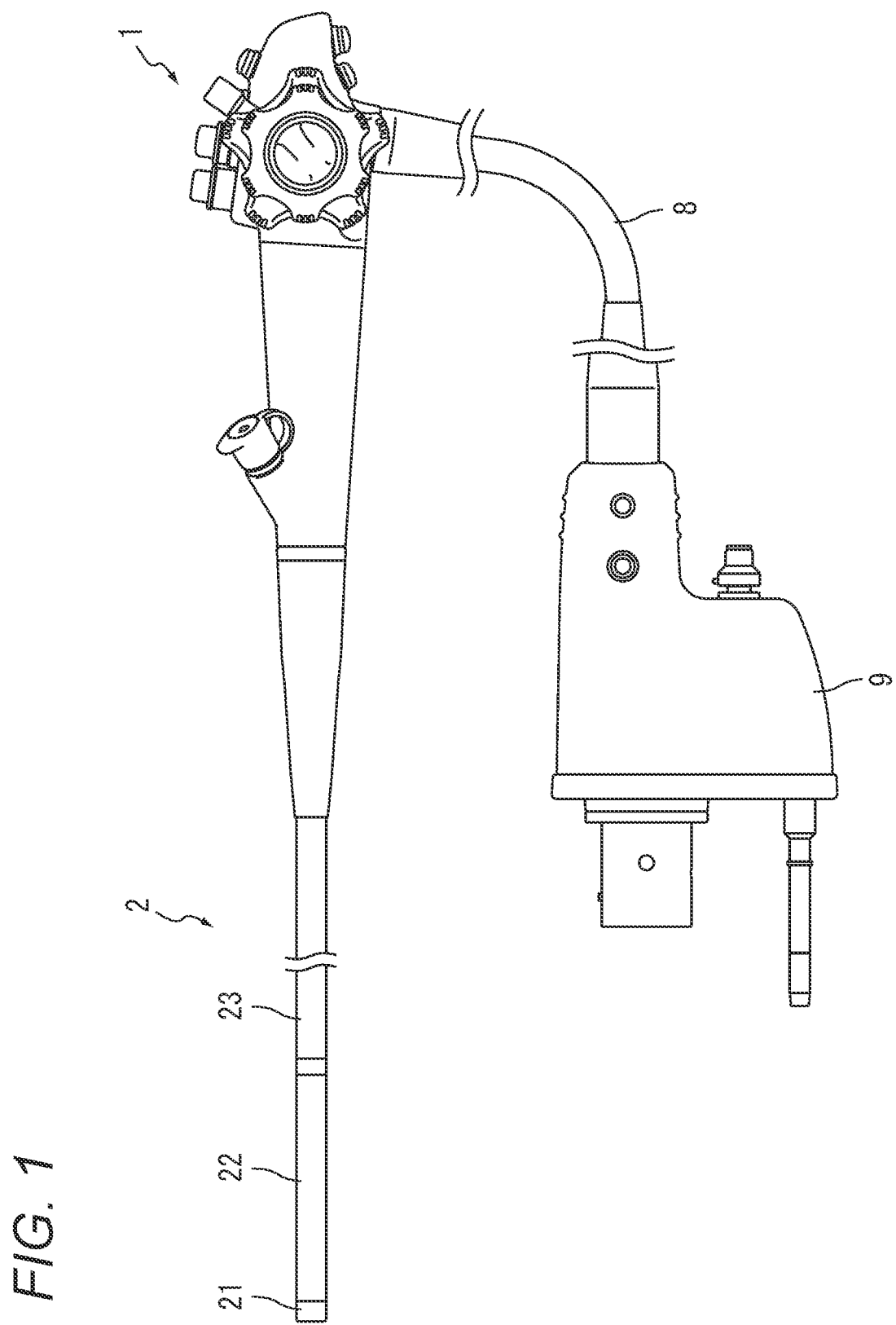
FIG. 1 is a schematic view illustrating an overall configuration of an endoscope according to the present embodiment.

FIG. 1 is a schematic view illustrating an overall configuration of an endoscope according to the present embodiment. The endoscope according to the present embodiment includes an operation unit 1 held by an operator and an insertion portion 2 extending from the operation unit 1.

The insertion portion 2 includes a flexible tube 23 that is sheathed with a flexible sheath (outer skin). At the distal end of the flexible tube 23, a distal end portion 21 sheathed with a rigid resin casing is joined. A bending section 22 provided at a joint between the flexible tube 23 and the distal end portion 21 is configured to bend in a direction intersecting an optical axis direction of the endoscope when operated on the operation unit 1. This bending mechanism is a known mechanism incorporated in a typical endoscope, and is configured such that the bending section 22 is bent by pulling operation of an operation wire in conjunction with the operation of the operation unit 1 (specifically, rotation operation of a bending operation knob). An imaging region of the endoscope moves together with a change in the direction of the distal end portion 21 according to the bending operation by the above operation.

The operation unit 1 includes the bending operation knob for bending the bending section 22, and also includes an air/water supply button for ejecting gas or liquid from the distal end portion 21, a freeze button to switch an observation image to a moving image display or a still image display, a freeze button, a zoom button for instructing enlargement/reduction of the observation image, a switching button for switching between normal light and treatment light, or the like.

In addition, a connector unit 9 is connected to the operation unit 1 via a universal cord 8. The endoscope is electrically and optically connected to a processor device (not illustrated) via the connector unit 9. The processor device is a device that integrally includes a signal processing device that processes an image signal from an endoscope and a light source device that irradiates, via the endoscope, a body cavity having difficulty receiving natural light. In another embodiment, the signal processing device and the light source device may be provided separately. The processor device outputs a processed image signal to an external monitor device (not illustrated) and displays an observation image on the monitor device.

Figure 2:
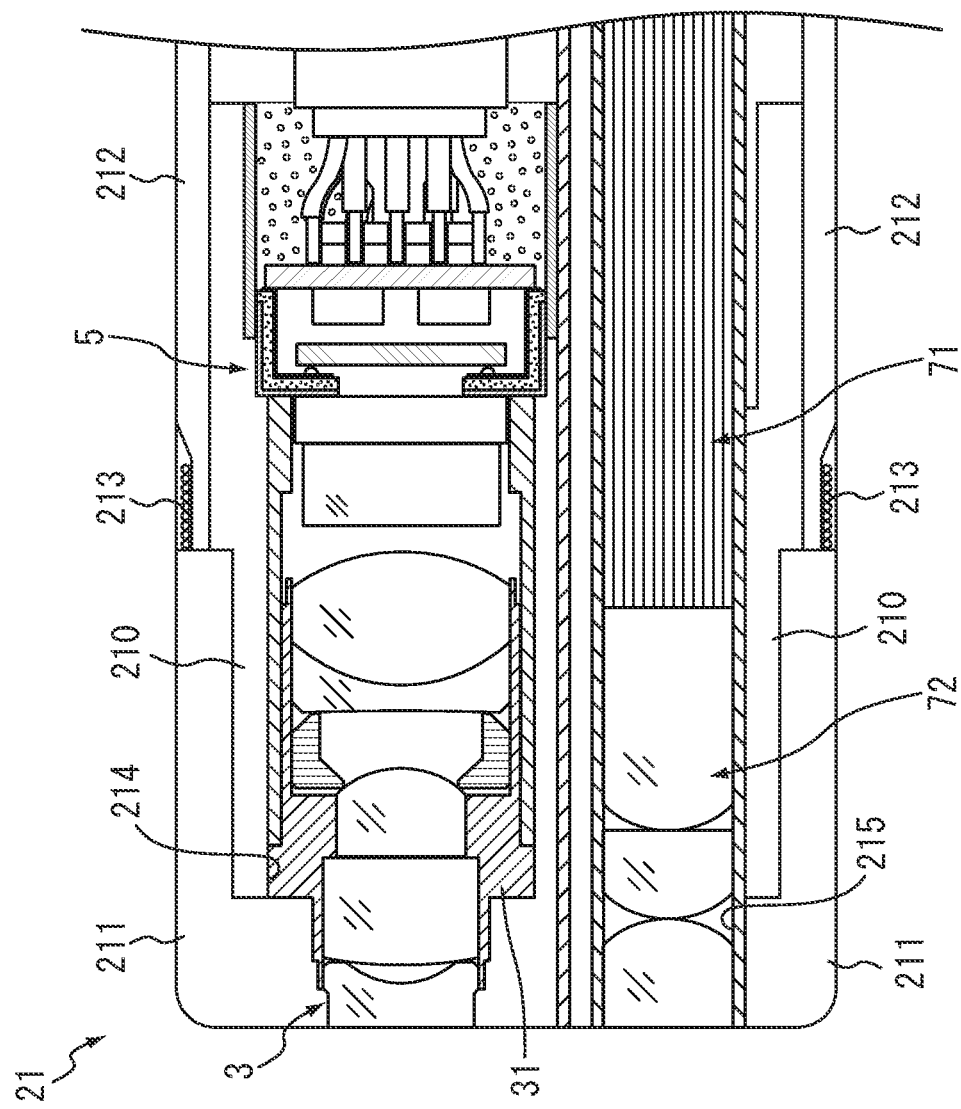
FIG. 2 is a schematic cross-sectional view illustrating an internal configuration of a distal end portion.

FIG. 2 is a schematic cross-sectional view illustrating an internal configuration of the distal end portion 21. FIG. 2 illustrates a cross section obtained by cutting the distal end portion 21 along the optical axis of a lens unit 3 and an imaging unit 5. In the following description, the distal end side of the insertion portion 2 is also referred to as "front" of the endoscope, and the proximal end side (operation unit 1 side) of the insertion portion 2 is also referred to as "rear of" or "behind" the endoscope.

The distal end portion 21 includes a cylindrical distal end portion main body 210 formed of a metal or resin having high rigidity and satisfactory thermal conductivity, and a distal end portion cover 211 that is fitted to the front side of the distal end portion main body 210. On the outer peripheral surface on the rear side of the distal end portion main body 210, a bending rubber member 212 constituting the bending section 22 is disposed. The bending rubber member 212 is secured to the distal end portion main body 210 by a binding thread 213 with low elasticity, and further secured with an adhesive, thereby ensuring watertightness in the insertion portion 2.

Figure 4:
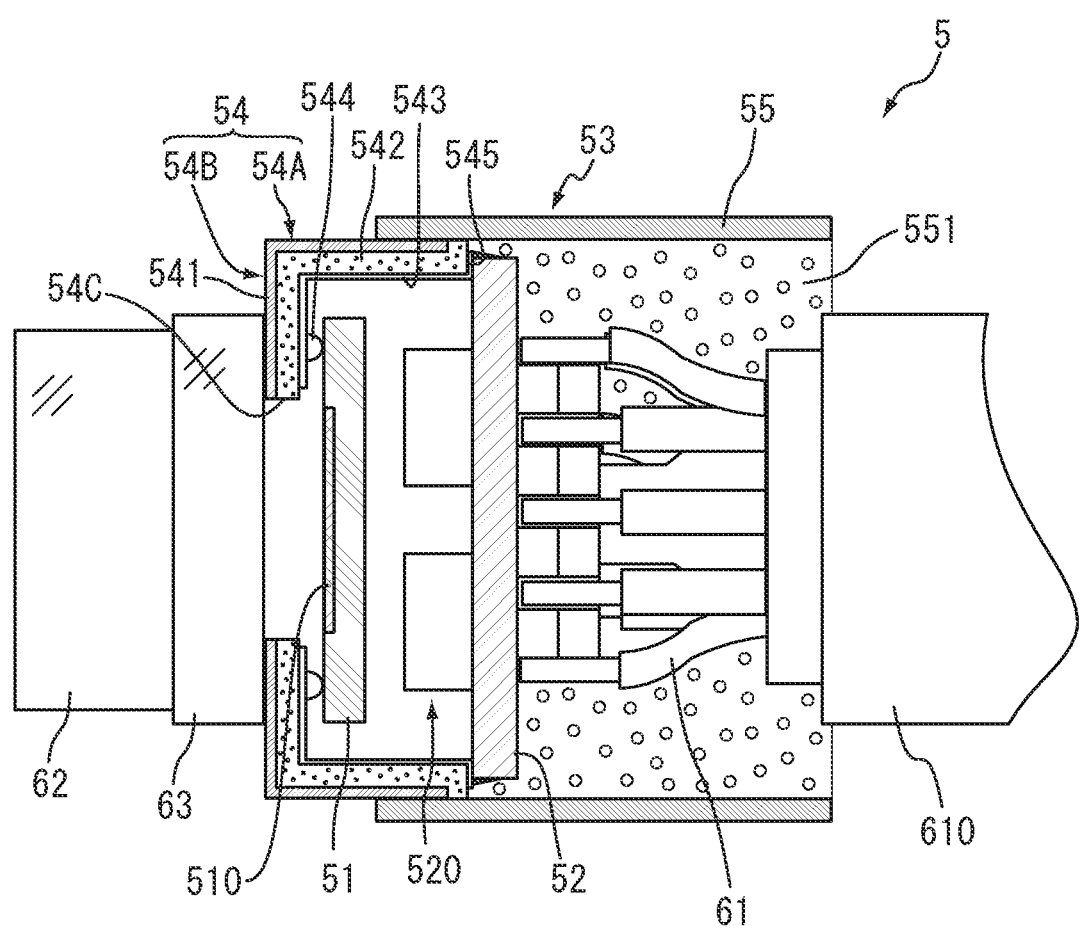
FIG. 4 is an enlarged cross-sectional view of an imaging unit.

The distal end portion main body 210 includes a housing space 214 that houses the lens unit 3 including a plurality of objective lenses and houses the imaging unit 5 including electronic components such as an image sensor 51 (refer to FIG. 4). This housing space 214 has a rectangular cross section, for example. The lens unit 3 is disposed in the housing space 214 via a lens frame 31 for arranging each of the objective lenses at a predetermined position. The imaging unit 5 is secured in the housing space 214 with an adhesive having satisfactory thermal conductivity at a position behind the lens unit 3.

The distal end portion 21 includes a housing space 215 that houses a light guide 71, together with the housing space 214. The housing space 215 has a circular cross section, for example. A distal end portion of a light guide 71 formed of a plurality of optical fibers is secured in the housing space 215. In front of the light guide 71, there is provided an illumination optical lens group 72 that emits illumination light guided by the light guide 71 from the light source device.

Hereinafter, a configuration of the imaging unit 5 will be described.

Figure 3:
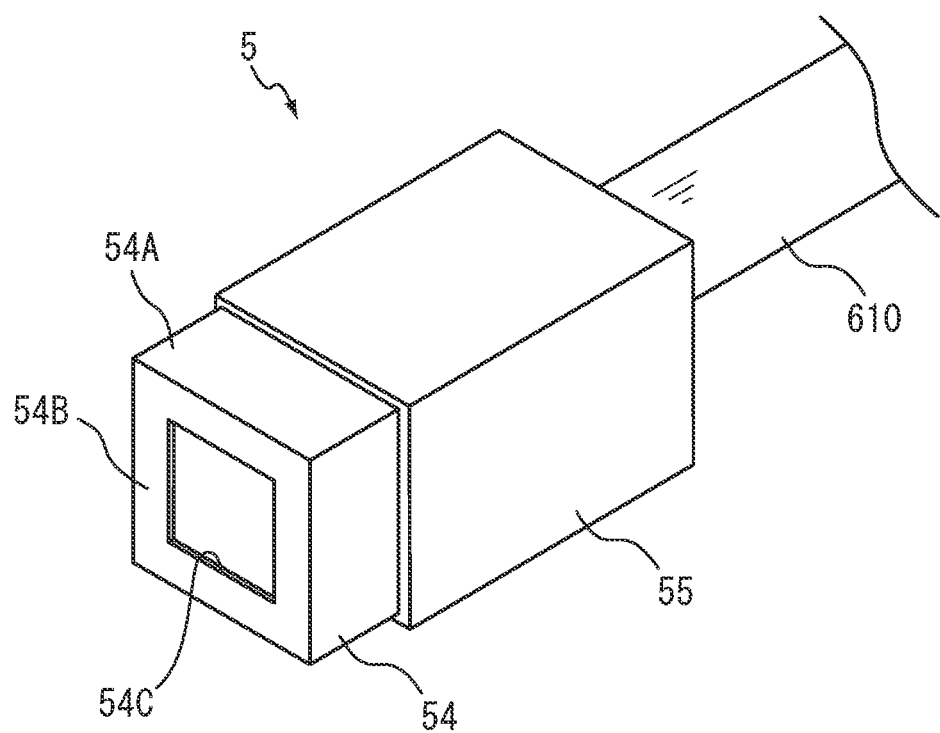
FIG. 3 is an external perspective view of an imaging unit.

FIG. 3 is an external perspective view of the imaging unit 5. FIG. 4 is an enlarged cross-sectional view of the imaging unit 5. The imaging unit 5 includes: an image sensor 51 having a light receiving area 510 formed of a photodiode on a surface facing the lens unit 3 including the objective lens; a drive circuit substrate 52 mounted behind the image sensor 51 and includes, on the substrate, a drive circuit 520 that drives the image sensor 51; an electromagnetic shield 53 that houses the image sensor 51 and the drive circuit substrate 52; a bandpass filter 62; and a glass cover 63. Note that FIG. 3 omits illustration of the bandpass filter 62 and the glass cover 63.

The image sensor 51 has an appropriate thickness and is disposed in the electromagnetic shield 53 so that the light receiving area 510 is substantially orthogonal to the optical axis direction of the lens unit 3. On the front surface of the image sensor 51, a bonding pad (not illustrated) is formed together with a light receiving area 510 and a plurality of circuits. The image sensor 51 is a photoelectric conversion element such as a complementary metal oxide semiconductor (CMOS) image sensor or a charge coupled device (CCD), for example. The image sensor 51 extracts electric charges accumulated according to the light quantity of the optical image formed in the light receiving area 510, converts the charge into an imaging signal (electrical signal), and outputs the signal to the outside through the bonding pad.

The drive circuit substrate 52 is a rectangular substrate having an appropriate thickness, and is disposed behind the image sensor 51 in the electromagnetic shield 53 so that the substrate surface is substantially parallel to the substrate surface of the image sensor 51. On the front surface of the drive circuit substrate 52, there are provided a drive circuit 520 including electronic circuit components such as an integrated circuit (IC), a capacitor, and a resistor, and a wiring pattern for electrically connecting these electronic circuit components. In addition, one end of each of cables 61 bundled as a composite cable 610 is connected to the rear surface of the drive circuit substrate 52. Each of the cables 61 of the composite cable 610 is connected to a part of a land 545 included in the drive circuit 520 on the front surface and a three-dimensional wiring layer 543 described below via a through-silicon via (not illustrated) penetrating through the drive circuit substrate 52, for example. The composite cable 610 is connected to the connector unit 9 through the bending section 22, the flexible tube 23, and the operation unit 1. The composite cable 610 transmits an imaging signal or the like output from the image sensor 51 to the processor device via the connector unit 9 as well as transmitting a control signal input from the processor device via the connector unit 9 to the drive circuit substrate 52 and the image sensor 51.

The electromagnetic shield 53 includes a front shield member 54 located on the front side (distal end side), and a rear shield member 55 externally fitted on the rear end portion of the front shield member 54. The electromagnetic shield 53 houses the image sensor 51 and the drive circuit substrate 52 in an internal space formed by the front shield member 54 and the rear shield member 55, and ensures electromagnetic compatibility. The electromagnetic shield 53 is preferably grounded through a wire (not illustrated).

The front shield member 54 includes: a cylinder 54A having a rectangular cross section and covering the side portion of the image sensor 51; and a structure 54B connected to the front end portion of the cylinder 54A and is arranged between the lens unit 3 and the image sensor 51. The structure 54B includes a rectangular opening 54C that exposes the light receiving area 510 formed on the front surface of the image sensor 51 and that allows entrance of light from the lens unit 3.

The bandpass filter 62 and the glass cover 63 are provided in front of the front shield member 54. The bandpass filter 62 transmits light in a specific wavelength region and blocks transmission of light in other wavelength regions. In the present embodiment, the bandpass filter 62 is provided to remove infrared light unnecessary in the endoscopic examination. The glass cover 63, an optical member having high light transmittance, is provided to cover the opening 54C between the bandpass filter 62 and the structure 54B of the front shield member 54 in order to prevent the light receiving area 510 from being damaged.

The cylinder 54A and the structure 54B constituting the front shield member 54 are integrally formed by a metal base 541 and an insulating layer 542 disposed on the inner peripheral surface side of the base 541. The base 541 is formed of a conductive material such as stainless steel or brass, and has a thickness of approximately 0.05 mm to 0.1 mm, for example. In contrast, the insulating layer 542 is formed by application of an insulating resin to the inner peripheral surface of the base 541, and has a thickness of approximately 0.2 mm to 0.5 mm, for example. The insulating resin applied to the base 541 is preferably a material having high adhesion to the three-dimensional wiring layer 543 (metal wiring) described below.

The bump 544 is provided at a site of the structure 54B that face the bonding pad of the image sensor 51. The image sensor 51 is mounted in the internal space of the front shield member 54 by flip chip mounting via the bump 544. The bump 544 may be provided on the bonding pad of the image sensor 51. The land 545 is formed on the rear end surface of the cylinder 54A so as to face a predetermined site of a wiring pattern (not illustrated) formed on the front surface of the drive circuit substrate 52. The drive circuit substrate 52 is mounted on the rear end surface of the cylinder 54A by means of soldering or the like so as to provide conductivity between a predetermined site of the wiring pattern and the land 545.

In the present embodiment, with the presence of the three-dimensional wiring layer 543 provided on the inner peripheral surface of the front shield member 54 (insulating layer 542), it is possible to ensure conductivity between the bump 544 on the image sensor 51 side and the land 545 on the drive circuit substrate 52 side. The three-dimensional wiring layer 543 is formed by selectively depositing metal on the inner peripheral surface of the front shield member 54 by a selective plating method using laser processing or a selective plating method using a resist pattern.

Since the bump 544 on the image sensor 51 side and the land 545 on the drive circuit substrate 52 side are connected via the three-dimensional wiring layer 543, the imaging signal output by the image sensor 51 is transmitted to the drive circuit substrate 52 via the three-dimensional wiring layer 543, and further transmitted to the processor device via the cable 61 connected to the drive circuit substrate 52. The control signal input from the processor device via the cable 61 is transmitted to a wiring pattern formed on the front surface of the drive circuit substrate 52 through a through-silicon via (not illustrated) and then transmitted to the image sensor 51 via the three-dimensional wiring layer 543 connected to a predetermined site of the wiring pattern.

In the present embodiment, the base 541 of the front shield member 54 is formed of metal. However, the base 541 formed of a molded resin or ceramic may also be used. In this case, a solid GND pattern (conductive layer) may be provided on the outer peripheral surface of the resin or ceramic base to ensure the shielding function.

In the present embodiment, the cylinder 54A and the structure 54B are integrally formed. However, the cylinder 54A and the structure 54B may be separately provided.

The rear shield member 55 is a cylinder having a rectangular cross section, and has a size that can be fitted into the rear end portion of the front shield member 54. The cylindrical wall of the rear shield member 55 is formed of a conductive material such as stainless steel or brass, and has a thickness of approximately 0.05 mm to 0.1 mm, for example. After the image sensor 51 and the drive circuit substrate 52 are mounted on the front shield member 54, and each of the cables 61 constituting the composite cable 610 is connected to the rear surface of the drive circuit substrate 52, the rear shield member 55 is externally fitted to the rear end portion of the front shield member 54 so as to overlap by an appropriate width in the front/rear direction, and then secured by means such as adhesion or soldering.

In addition, the internal space of the rear shield member 55 from the side surface and rear surface of the drive circuit substrate 52 to the opening end of the rear shield member 55 is filled with a resin agent 551 (filler) having an insulating property and satisfactory thermal conductivity. As a result, each cable 61 constituting the drive circuit substrate 52 and the composite cable 610 is secured inside the rear shield member 55.

As described above, according to the present embodiment, it is possible to reduce the size in the direction (plane direction) orthogonal to the optical axis direction, as compared with the conventional packaging that employs wire bonding. Furthermore, since the three-dimensional wiring layer 543 is provided on the inner peripheral surface of the electromagnetic shield 53, there is no need to bend the copper foil circuit as in the TAB structure, leading to reduction of the risk of disconnection.

Second Embodiment

In a second embodiment, a description will be given of a configuration of providing a cutout portion (half-cut through hole) cut out in the surface direction in a part of the drive circuit substrate 52.

Figure 5:
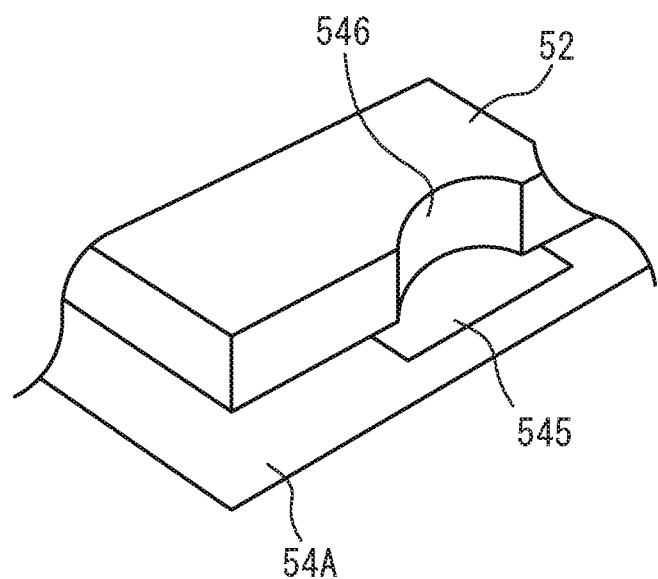
FIG. 5 is a partial enlarged view illustrating a configuration of a drive circuit substrate according to a second embodiment.

FIG. 5 is a partially enlarged view illustrating a configuration of the drive circuit substrate 52 according to the second embodiment. As described above, the land 545 electrically connected to the image sensor 51 is provided on the rear end surface of the front shield member 54. The drive circuit substrate 52 in the second embodiment includes a half-cut through hole 546 obtained by cutting the periphery of the substrate in the thickness direction so as to expose a part of the land 545 formed on the rear end surface of the front shield member 54.

In the second embodiment, since it is possible to expose a part of the land 545 formed on the rear end surface of the front shield member 54 in a state where the drive circuit substrate 52 is mounted on the front shield member 54, a part of the cable 61 constituting the composite cable 610 can be connected to the land 545. With this configuration, it is possible, in the second embodiment, to directly extract the wires from the terminal (for example, the ground terminal) of the image sensor 51 that does not need to go through the drive circuit substrate 52. Alternatively, it is allowable to adopt a configuration in which solder is applied to the half-cut through hole 546 to solder the drive circuit substrate 52 and the front shield member 54.

Third Embodiment

In a third embodiment, another example of implementation of the drive circuit substrate 52 will be described.

Figure 6:
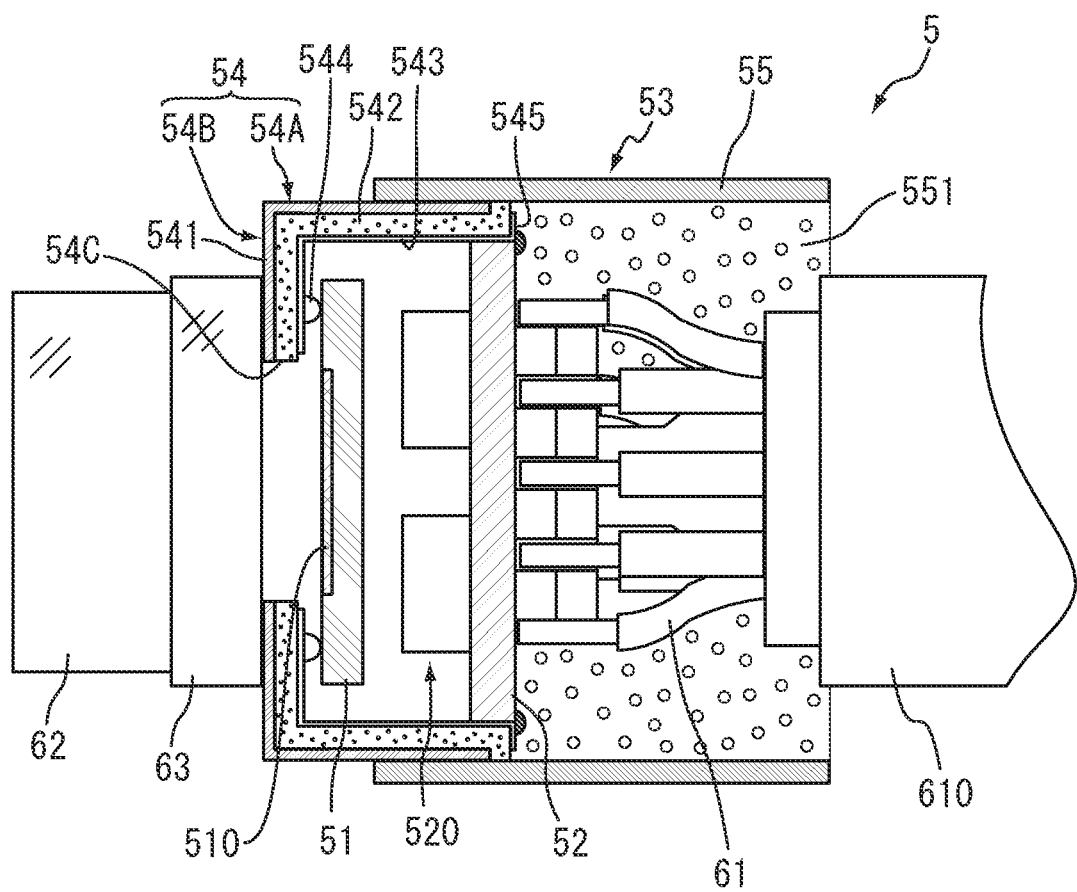
FIG. 6 is an enlarged cross-sectional view of an imaging unit according to a third embodiment.

FIG. 6 is an enlarged cross-sectional view of the imaging unit 5 according to the third embodiment. The imaging unit 5 according to the third embodiment includes the image sensor 51 having a light receiving area 510 formed on a surface facing the lens unit 3 including the objective lens; the drive circuit substrate 52 mounted behind the image sensor 51 and includes, on the substrate, the drive circuit 520 that drives the image sensor 51; the electromagnetic shield 53 that houses the image sensor 51 and the drive circuit substrate 52; the bandpass filter 62; and the glass cover 63.

The electromagnetic shield 53 includes the front shield member 54 and the rear shield member 55 similarly to the first embodiment. The cylinder 54A of the front shield member 54 has an inner diameter that is slightly larger than the size of the drive circuit substrate 52 in the surface direction. In the third embodiment, the drive circuit substrate 52 is mounted on the cylinder 54A in a state where the side surface of the drive circuit substrate 52 and the inner peripheral surface near the rear end portion of the cylinder 54A face each other. Specifically, the rear surface of the drive circuit substrate 52 and the rear end surface of the cylinder 54A are soldered, whereby the drive circuit substrate 52 is mounted on the cylinder 54A.

In the present embodiment, a part of the wiring pattern for the drive circuit 520 may be formed on the rear surface of the drive circuit substrate 52, and this wiring pattern may be connected to the drive circuit 520 through a through-silicon via (not illustrated) while connecting the wiring pattern formed on the rear surface of the drive circuit substrate 52 to the land 545 on the rear end surface of the cylinder. In this case, it is possible to ensure, between the drive circuit 520 mounted on the drive circuit substrate 52 and the image sensor 51, implementation of a conduction path that passes through the wiring pattern formed on the front surface of the drive circuit substrate 52, the through-silicon via, the wiring pattern formed on the rear surface of the drive circuit substrate 52, the land 545, the three-dimensional wiring layer 543, and the bump 544. It is then possible to perform signal transmission and reception through this conduction path.

As described above, the drive circuit substrate 52, in the third embodiment, is mounted on the cylinder 54A in a state where the side surface of the drive circuit substrate 52 and the inner peripheral surface near the rear end portion of the cylinder 54A face each other. This makes it possible to receive an external force acting in the in-plane direction from the outside of the electromagnetic shield 53 by the side surface of the drive circuit substrate 52, enabling improvement of the strength of the electromagnetic shield 53.

Fourth Embodiment

In a fourth embodiment, a configuration in which a drive circuit is mounted on the rear surface of the drive circuit substrate 52 will be described.

Figure 7:
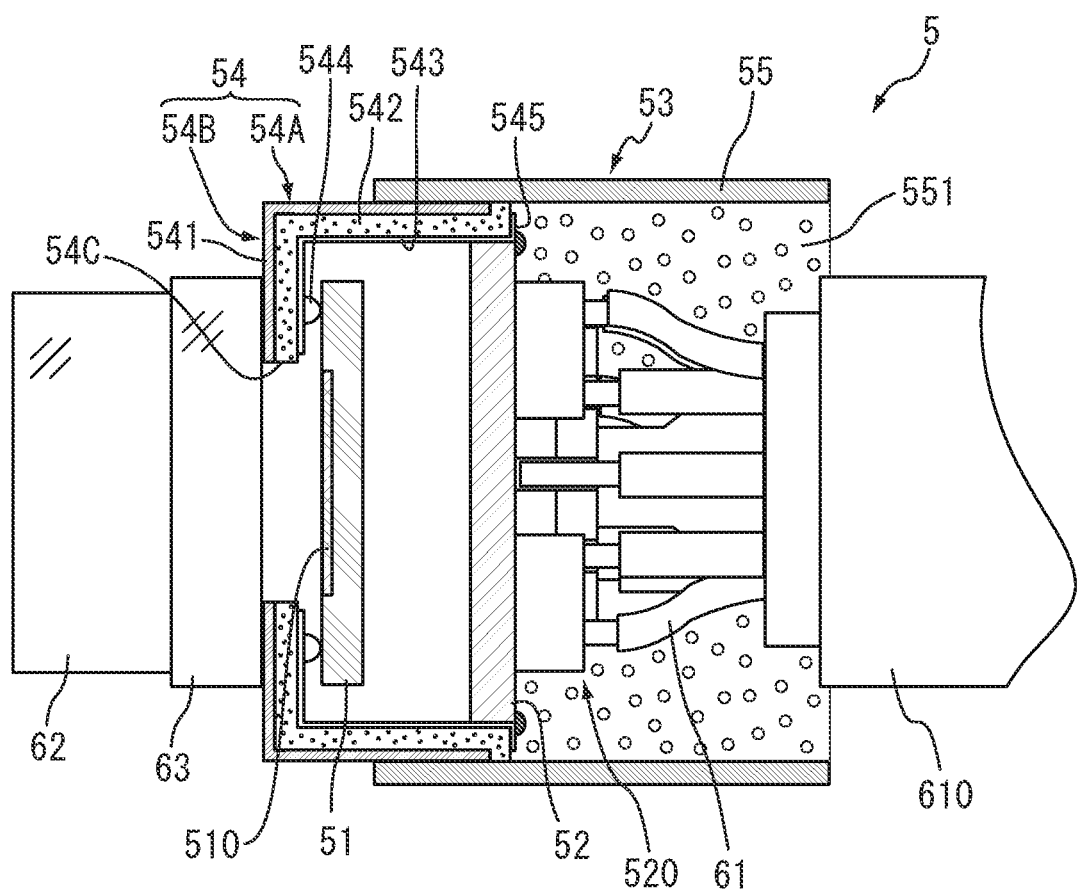
FIG. 7 is an enlarged cross-sectional view of an imaging unit according to a fourth embodiment.

FIG. 7 is an enlarged cross-sectional view of the imaging unit 5 according to the fourth embodiment. The imaging unit 5 according to the fourth embodiment includes the image sensor 51 having a light receiving area 510 formed on a surface facing the lens unit 3 including the objective lens; the drive circuit substrate 52 mounted behind the image sensor 51 and includes, on the substrate, the drive circuit 520 that drives the image sensor 51; the electromagnetic shield 53 that houses the image sensor 51 and the drive circuit substrate 52, the bandpass filter 62, and the glass cover 63.

The electromagnetic shield 53 includes the front shield member 54 and the rear shield member 55 similarly to the first embodiment. The cylinder 54A of the front shield member 54 has an inner diameter that is slightly larger than the size of the drive circuit substrate 52 in the surface direction. In the third embodiment, the drive circuit substrate 52 is mounted on the cylinder 54A in a state where the side surface of the drive circuit substrate 52 is in contact with the inner peripheral surface near the rear end portion of the cylinder 54A. Specifically, the rear surface of the drive circuit substrate 52 and the rear end surface of the cylinder 54A are soldered, whereby the drive circuit substrate 52 is mounted on the cylinder 54A.

In the present embodiment, the drive circuit 520 including a wiring pattern may be formed on the rear surface of the drive circuit substrate 52, and this wiring pattern may be connected to the land 545 on the rear end surface of the cylinder. In this case, it is possible to ensure, between the drive circuit 520 mounted on the drive circuit substrate 52 and the image sensor 51, implementation of a conduction path that passes through the wiring pattern formed on the rear surface of the drive circuit substrate 52, the land 545, the three-dimensional wiring layer 543, and the bump 544. It is then possible to perform signal transmission and reception via this conduction path.

As described above, the drive circuit substrate 52, in the fourth embodiment, is mounted on the cylinder 54A in a state where the side surface of the drive circuit substrate 52 is in contact with the inner peripheral surface near the rear end portion of the cylinder 54A. This makes it possible to receive an external force acting in the in-plane direction from the outside of the electromagnetic shield 53 by the side surface of the drive circuit substrate 52, enabling improvement of the strength of the electromagnetic shield 53.

In the fourth embodiment, the drive circuit 520 is mounted on the rear surface side of the drive circuit substrate 52. Accordingly, it is possible to keep the drive circuit 520 being a heat generation source away from the image sensor 51, and possible to efficiently dissipate the heat generated in the drive circuit 520, by the resin agent 551 filled in the internal space of the rear shield member 55.

The embodiments disclosed herein are exemplary in all respects, and it should be considered that the embodiments are not restrictive. The scope of the present invention is defined not by the above-described meaning but by claims, and intends to include all modifications within meaning and a scope equal to claims.

REFERENCE SIGNS LIST

1 Operation unit
2 Insertion portion
3 Lens unit
5 Imaging unit
8 Universal cord
9 Connector unit
21 Distal end portion
22 Bending section
23 Flexible tube
51 Image sensor
52 Drive circuit substrate
53 Electromagnetic shield
54 Front shield member
54A Cylinder
54B Structure
61 Cable
62 Bandpass filter
63 Glass cover
510 Light receiving area
520 Drive circuit
541 Base
542 Insulating layer
543 Three-dimensional wiring layer
544 Bump
545 Land
546 Half-cut through hole
551 Resin agent
610 Composite cable

The invention claimed is:

1. An endoscope comprising:
an objective lens provided at a distal end portion of an insertion portion, an image sensor in which a light receiving area is formed on a surface facing the objective lens, and a drive circuit substrate that is disposed on a back side of the image sensor and includes a drive circuit to drive the image sensor,
the endoscope further comprising an electromagnetic shield that houses the image sensor and the drive circuit substrate,
wherein the electromagnetic shield includes:
a first shield member including
a cylinder that covers a side portion of the image sensor,
a structure that is disposed between the image sensor and the objective lens and that has an opening that allows entrance of light from the objective lens, and
a wiring pattern that is formed on an inner peripheral surface of the cylinder and the structure and provided to electrically connect the image sensor and the drive circuit substrate; and
a second shield member externally fitted on a rear end side of the first shield member.

2. The endoscope according to claim 1, further comprising:
a bump connected to one end of the wiring pattern and provided at a site of the structure facing the image sensor; and
a land connected to the other end of the wiring pattern and provided to ensure conduction with the drive circuit mounted on the drive circuit substrate.

3. The endoscope according to claim 2,
wherein the drive circuit substrate is mounted on the cylinder in a state where a front surface of the drive circuit substrate and a rear end surface of the cylinder face each other.

4. The endoscope according to claim 3,
wherein the drive circuit substrate includes a cutout portion cut out in a thickness direction of the drive circuit substrate so as to expose a part of the land.

5. The endoscope according to claim 2,
wherein the drive circuit substrate is mounted on the cylinder in a state where a side surface of the drive circuit substrate and an inner peripheral surface of the cylinder face each other.

6. The endoscope according to claim 2,
wherein the image sensor is mounted in the electromagnetic shield via the bump.

7. The endoscope according to claim 1,
wherein the cylinder and the structure are integrally formed and include a base formed of a conductive material and an insulating layer formed on an inner peripheral surface of the base.

8. The endoscope according to claim 1,
wherein the cylinder and the structure are integrally formed and include a base formed of an insulating material and a conductive layer formed on an outer peripheral surface of the base.

9. The endoscope according to claim 1,
wherein an internal space of the second shield member is filled with an insulating filler.

* * * * *